(12) United States Patent
Lederman et al.

(10) Patent No.: US 9,987,135 B2
(45) Date of Patent: Jun. 5, 2018

(54) DEVICES AND METHODS FOR TREATING FUNCTIONAL TRICUSPID VALVE REGURGITATION

(71) Applicant: The United States of America, as represented by the Secretary, Department of Health and Human Services, Washington, DC (US)

(72) Inventors: Robert J. Lederman, Chevy Chase, MD (US); Kanishka Ratnayaka, Washington, DC (US); Toby Rogers, Washington, DC (US)

(73) Assignee: The United States of America, as Represented by the Secretary, Department of Health and Human Services, Washington, DC (US)

(*) Notice: Subject to any disclaimer, the term of this patent is extended or adjusted under 35 U.S.C. 154(b) by 290 days.

(21) Appl. No.: 14/776,488

(22) PCT Filed: Mar. 13, 2014

(86) PCT No.: PCT/US2014/025300
§ 371 (c)(1),
(2) Date: Sep. 14, 2015

(87) PCT Pub. No.: WO2014/159842
PCT Pub. Date: Oct. 2, 2014

(65) Prior Publication Data
US 2016/0038287 A1    Feb. 11, 2016

Related U.S. Application Data

(60) Provisional application No. 61/785,652, filed on Mar. 14, 2013.

(51) Int. Cl.
*A61F 2/24* (2006.01)

(52) U.S. Cl.
CPC ......... *A61F 2/2481* (2013.01); *A61F 2/2442* (2013.01); *A61F 2002/2484* (2013.01); *A61F 2220/0016* (2013.01)

(58) Field of Classification Search
CPC ........ A61B 17/12009; A61B 17/12013; A61B 2017/00243; A61F 2/2442; A61F 2/2445;
(Continued)

(56) References Cited

U.S. PATENT DOCUMENTS 4,042,979 A * 8/1977 Angell .................. A61F 2/2448
623/2.37
4,048,990 A * 9/1977 Goetz ................. A61M 1/1062
601/153
(Continued)

FOREIGN PATENT DOCUMENTS

WO  WO 2008/060553  5/2008
WO  WO 2012/043898  4/2012

OTHER PUBLICATIONS

International Search Report and Written Opinion for International Application No. PCT/US2014/025300, 5 pages, dated Jul. 22, 2014.
(Continued)

*Primary Examiner* — Ryan J Severson
(74) *Attorney, Agent, or Firm* — Klarquist Sparkman, LLP

(57) ABSTRACT

Disclosed here are devices and methods for treating functional tricuspid valve regurgitation and related conditions. Disclosed devices are adapted for applying force to an area of a patient's heart along or near the atrioventricular groove, and can include a tensioning element configured to be delivered by a flexible member guided through a catheter and positioned generally along or near the atrioventricular groove, and a compression member positionable along the tensioning element and over a desired segment of the atrioventricular groove to develop force to be applied to an (Continued)

adjacent area of the heart by selective tensioning of the tensioning element.

29 Claims, 8 Drawing Sheets

(58) Field of Classification Search
CPC .... A61F 2/2466; A61F 2/2478; A61F 2/2481; A61F 2002/2484; A61F 2220/0016
See application file for complete search history.

(56) References Cited

U.S. PATENT DOCUMENTS

| | | | | |
|---|---|---|---|---|
| 4,690,134 A * | 9/1987 | Snyders | A61M 1/1068 | 601/153 |
| 4,936,857 A * | 6/1990 | Kulik | A61F 2/2481 | 623/3.1 |
| 5,131,905 A * | 7/1992 | Grooters | A61M 1/1068 | 600/16 |
| 5,256,132 A * | 10/1993 | Snyders | A61B 17/00234 | 600/16 |
| 5,383,840 A * | 1/1995 | Heilman | A61M 1/1068 | 600/17 |
| 5,702,343 A * | 12/1997 | Alferness | A61F 2/2481 | 600/37 |
| 5,713,954 A * | 2/1998 | Rosenberg | A61F 2/2481 | 600/17 |
| 6,045,497 A * | 4/2000 | Schweich, Jr. | A61B 17/00234 | 128/898 |
| 6,050,936 A * | 4/2000 | Schweich, Jr. | A61B 17/00234 | 600/16 |
| 6,059,715 A * | 5/2000 | Schweich, Jr. | A61B 17/00234 | 128/898 |
| 6,077,218 A * | 6/2000 | Alferness | A61F 2/2481 | 600/37 |
| 6,126,590 A * | 10/2000 | Alferness | A61F 2/2481 | 600/37 |
| 6,165,121 A * | 12/2000 | Alferness | A61F 2/2481 | 600/37 |
| 6,165,122 A * | 12/2000 | Alferness | A61F 2/2481 | 600/37 |
| 6,179,791 B1 * | 1/2001 | Krueger | A61B 5/107 | 33/512 |
| 6,375,608 B1 * | 4/2002 | Alferness | A61F 2/2481 | 600/37 |
| 6,544,168 B2 * | 4/2003 | Alferness | A61F 2/2481 | 600/37 |
| 6,592,619 B2 * | 7/2003 | Melvin | A61F 2/02 | 600/16 |
| 6,695,769 B2 * | 2/2004 | French | A61F 2/2481 | 600/37 |
| 6,701,929 B2 * | 3/2004 | Hussein | A61B 17/00234 | 128/898 |
| 7,144,363 B2 * | 12/2006 | Pai | A61B 17/00234 | 600/16 |
| 7,354,396 B2 * | 4/2008 | French | A61F 2/2481 | 600/37 |
| 7,361,191 B2 * | 4/2008 | Melvin | A61F 2/02 | 600/16 |
| 8,192,351 B2 * | 6/2012 | Fishler | A61B 17/00234 | 600/37 |
| 8,211,171 B2 * | 7/2012 | Kim | A61F 2/2451 | 623/2.37 |
| 8,231,671 B2 * | 7/2012 | Kim | A61F 2/2451 | 606/144 |
| 8,382,653 B2 * | 2/2013 | Dubi | A61B 17/00234 | 267/154 |
| 8,771,297 B2 * | 7/2014 | Miller | A61B 17/12013 | 606/113 |
| 9,271,833 B2 * | 3/2016 | Kim | A61F 2/2451 | |
| 9,579,200 B2 * | 2/2017 | Lederman | A61B 17/00234 | |
| 2001/0014811 A1 * | 8/2001 | Hussein | A61B 17/00234 | 606/151 |
| 2002/0007216 A1 * | 1/2002 | Melvin | A61F 2/02 | 623/3.11 |
| 2003/0060677 A1 * | 3/2003 | French | A61F 2/2481 | 600/37 |
| 2003/0078465 A1 * | 4/2003 | Pai | A61B 17/00234 | 600/16 |
| 2004/0024286 A1 * | 2/2004 | Melvin | A61F 2/02 | 600/16 |
| 2004/0097787 A1 * | 5/2004 | French | A61F 2/2481 | 600/37 |
| 2005/0216039 A1 * | 9/2005 | Lederman | A61B 17/0469 | 606/144 |
| 2008/0243183 A1 * | 10/2008 | Miller | A61B 17/12013 | 606/228 |
| 2010/0022821 A1 * | 1/2010 | Dubi | A61B 17/00234 | 600/37 |
| 2010/0049314 A1 * | 2/2010 | Kim | A61F 2/2451 | 623/2.37 |
| 2010/0081867 A1 * | 4/2010 | Fishler | A61B 17/00234 | 600/37 |
| 2011/0015478 A1 * | 1/2011 | Vanden Hoek | A61F 2/2481 | 600/37 |
| 2011/0054597 A1 * | 3/2011 | Kim | A61F 2/2451 | 623/2.37 |
| 2012/0232574 A1 * | 9/2012 | Kim | A61F 2/2451 | 606/191 |
| 2013/0211510 A1 * | 8/2013 | Lederman | A61B 17/00234 | 623/2.11 |
| 2016/0038287 A1 * | 2/2016 | Lederman | A61F 2/2442 | 623/2.11 |
| 2016/0120647 A1 * | 5/2016 | Rogers | A61F 2/2481 | 606/139 |
| 2016/0242908 A1 * | 8/2016 | Kim | A61F 2/2451 | |

OTHER PUBLICATIONS

Rogers et al., "Trans-Auricular Intra-Pericardial Tricuspid Annuloplasty (TRAIPTA)," *Journal of the American College of Cardiology*, 62(18):B41 (Oct. 28, 2013).

* cited by examiner

DEVICES AND METHODS FOR TREATING FUNCTIONAL TRICUSPID VALVE REGURGITATION

CROSS REFERENCE TO RELATED APPLICATIONS

This is the U.S. National Stage of International Application No. PCT/US2014/025300, filed Mar. 13, 2014, which was published in English under PCT Article 21(2), and which claims the benefit of U.S. Provisional Application No. 61/785,652, filed Mar. 14, 2013. The provisional application is incorporated herein in its entirety.

FIELD

This application is related to devices and methods for treating tricuspid valve regurgitation, including devices and methods for tricuspid valve annuloplasty.

BACKGROUND

Tricuspid valve regurgitation is a condition in which one of the valves of the heart "leaks" causing right ventricular blood to flow backwards into the right atrium. Commonly this occurs because the tricuspid valve annulus dilates beyond its ideal size. Addressing the condition is difficult because surgical tricuspid valve replacement is invasive and associated with significant morbidity and even mortality. Moreover, prosthetic tricuspid valves are prone to serious complications including thrombosis and infection, which makes the valve replacement approach less desirable.

It would be advantageous to develop approaches to addressing tricuspid valve regurgitation and other similar conditions of the heart that do not require replacement of organs or their components and minimize the risks presented by invasive surgery.

SUMMARY

Described below are new approaches to treating functional tricuspid valve regurgitation that address some of the limitations and risks of conventional approaches.

According to one implementation, a device for tricuspid valve annuloplasty or other procedure in the area of the heart's atrioventricular groove comprises a tensioning element and a compression member. The tensioning element can be configured to be delivered by a flexible member guided through a catheter and positioned along or near the heart's atrioventricular groove. The compression member is positionable along the tensioning element and over a desired segment of the atrioventricular groove to develop force to be applied to an adjacent area of the heart by selective tensioning of the tensioning element.

The device can be deliverable through a catheter via the vasculature through the right atrium or right atrial appendage, or inserted along a trans-thoracic or subxiphoid or subcostal path. The compression member can be positionable along the tensioning element by using a capture device securable to the compression device to move the compression device relative to the tensioning element.

The compression member can be tubular and define a bore dimensioned to allow the tensioning element to pass through the compression member. In some implementations, the compression member has a groove dimensioned to receive the tensioning element and to assist in retaining contact between the tensioning element and the compression member.

The compression member can have at least one anti-slip feature configured to contact a surface to reduce slipping of the compression member relative to the heart when the compression member is in position over the desired segment with tension applied to the tensioning element. The anti-slip feature can comprise protruding barbs configured to an exterior surface of the heart.

The compression member can have a shaped profile along its length. The shaped profile can comprise at least two bends, at least one arch, an M-shaped portion and/or at least two inflection points between the segments of different curvatures.

The compression member can have a generally curved center segment, a generally straight center segment, and/or a center segment having a vertex.

The compression member can have end segments shaped to orient the compression member. The compression member can be self-orienting upon application of tension in a selected location for treatment. The compression element can be shaped such that the compression element is urged into a position normal to the treatment location as tension applied through the tensioning element is increased. The compression member can be comprised of multiple component parts separately deliverable through the catheter and configured to be assembled together near a treatment site.

The compression member can be resiliently deformable such that the compression member changes from a delivery shape suitable for delivery to a final shape after delivery to a treatment site is complete. The compression member can be at least partially defined by a first major radius of curvature and a second minor radius of curvature.

The device can comprise a protection member shaped to provide a protected space at least partially accommodating a blood vessel or other vital structure and to receive the tensioning element, wherein the protection member distributes force developed through increased tension in the tensioning element to either side of the protected space. As just two examples, the protection member can be configured for positioning over a coronary artery, or over a pulmonary artery trunk.

According to another implementation, a method of using the device for tricuspid annuloplasty comprises positioning the tensioning element around the heart and generally along the heart's atrioventricular groove, positioning the compression member along the tensioning element an opposite a desired treatment location and applying force to the desired treatment location with the compression element by applying tension with the tensioning.

Imaging guidance can be used to ascertain positions of at least one of the catheter, the compression member, and the tensioning element.

The method can comprise positioning at least one compression member along the tensioning element along a desired segment of the atrioventricular groove, the compression member applying force to a desired area of the heart with increasing tension in the tensioning element. The method can comprise delivering the compression member through the catheter and through an opening in the right atrial appendage. The method can comprise delivering multiple compression member components to the treatment area and assembling the compression member components into the compression member.

The method can comprise delivering the compression member through the catheter and through the right atrium or an opening in the right atrial appendage.

The method can comprise positioning at least one protection member along a segment of the tensioning element, the at least one protection member being shaped to provide a protected space at least partially accommodating a blood vessel or other vital structure.

The foregoing and other features and advantages will become more apparent from the following detailed description of several embodiments which proceeds with reference to the accompanying figures.

DETAILED DESCRIPTION

I. Explanation of Terms

Figure 1:
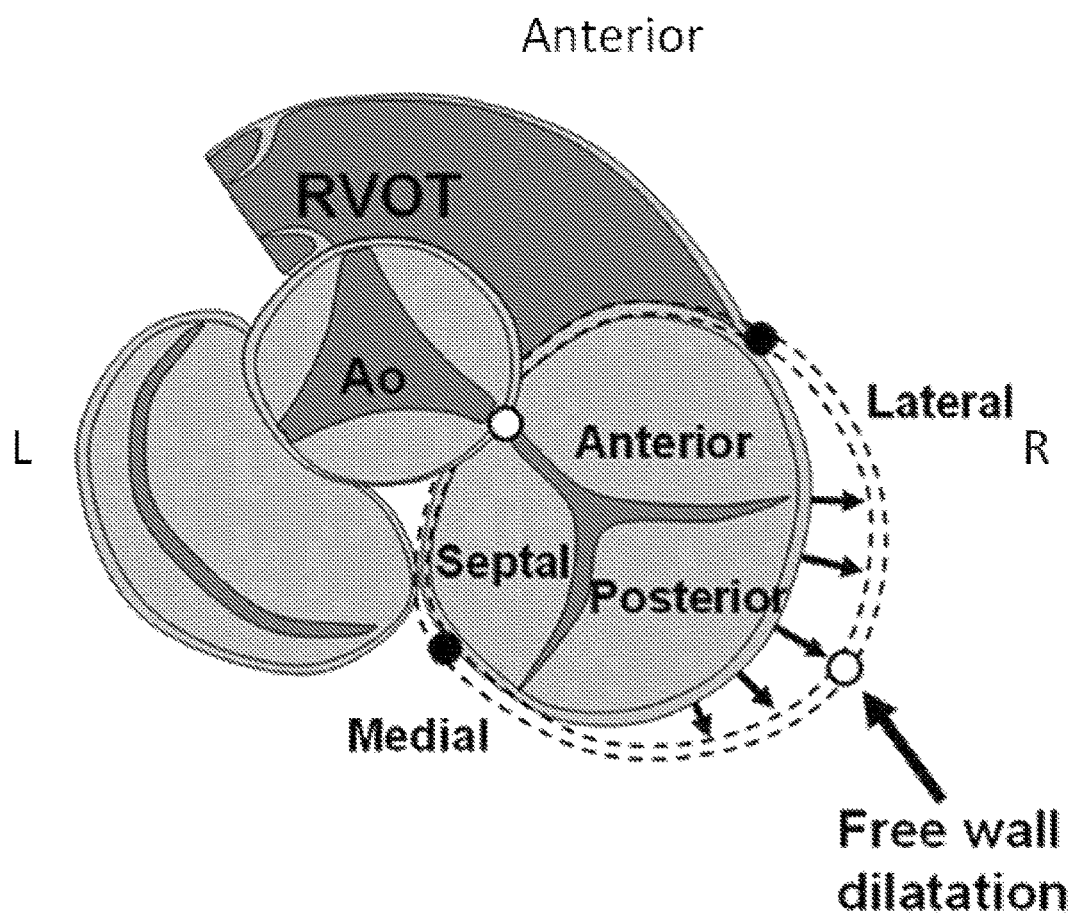
FIG. 1 is a schematic cross-sectional top plan view of a portion of a human heart, namely the tricuspid annulus, showing the annular dilation in dashed lines that causes functional tricuspid regurgitation.

Unless otherwise noted, technical terms are used according to conventional usage. In order to facilitate review of the various embodiments of the disclosure, the following explanation of terms is provided:

The term "comprises" means "includes without limitation." Thus, "comprising a tensioning element" means "including a tensioning element," without excluding additional elements.

A "device for tricuspid valve annuloplasty" refers to a device that induces reshaping of an annulus of the heart's tricuspid valve to repair valvular insufficiency. Such devices include those that are placed in contact with the annulus of the tricuspid valve, and include those that exert their action by compressive forces on the annulus, such as by placing a flexible annuloplasty member under tension, as in cerclage annuloplasty.

The term "flexible member" refers to an element that is sufficiently flexible to be introduced into the body, generally through a catheter, and manipulated along a desired path within the body, such as in and around the patient's heart. One example of such a flexible member is a "guide wire" of a conventional catheter, which can refer to a simple guide wire, a stiffened guide wire, or a steerable guide wire that is capable of puncturing and/or penetrating tissue, such as the right atrial appendage. The guide wire also can deliver energy to augment its ability to penetrate tissue, for example by puncturing it, delivering radiofrequency ablative energy or by delivering laser ablative energy.

As described below, the guide wire is used to position a separate "tensioning element" made of a suitable tensioning material generally along the heart's atrioventricular groove. Such a tensioning element is usually designed to remain deployed for the duration of the treatment. The tensioning element can be formed of any suitable tensioning material, including suture or ligature material or wire. The tensioning element may be comprised of segments made of different materials or having different properties, such as different elasticities. In some cases, the guide wire can also serve as the tensioning element.

A "capture device" is any suitable element or device that can be controlled, usually from outside the body, to engage the tensioning element (usually at a predetermined location along its length) to move and guide the tensioning element to a desired position and/or to manipulate it to increase its tension and the forces applied by it. For example, a capture device can be a conventional capture loop or a device having opposing members (like miniature forceps) that can pinch and hold the tensioning element.

The term "compression member" refers to an element that is designed to cooperate with the tensioning element to apply a desired force to an area along the path of the tensioning element. The compression member may be designed to provide a greater force to the area than would be applied by the tensioning element alone.

The term "protection member" refers to an element that is designed to cooperate with the tensioning element to provide a protected space to a blood vessel or other vital structure along the path of the tensioning element. In general, the protection member is designed so that the blood vessel or vital structure within the protection member experiences less force from the tensioning element than is exerted at adjacent areas at either end of the protection member.

In a "tricuspid valve annuloplasty" as described herein, a flexible member is placed around the annulus of the tricuspid valve, circumferential tension is developed in the flexible member or a tensioning element and resulting force is selectively applied around the tricuspid valve annulus. Examples of approaches to cerclage annuloplasty for a mitral valve are disclosed in U.S. Pat. No. 8,211,171, which is incorporated herein by reference. The described approaches include a cerclage trajectory through a proximal coronary septal perforator vein and myocardium or annulus fibrosis interposing between that vein and the right ventricle or right atrium to create circumferential cerclage annuloplasty tension.

The compression and protection members disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and non-magnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of a conflict, the present specification, including terms, will control. In addition, the materials, methods, and examples are illustrative only and not intended to be limiting.

II. Overview

One approach to tricuspid valve annuloplasty, or repair of the tricuspid valve, can be achieved by restricting dilation of the valve's free wall, which enhances coaptation or apposition of the tricuspid valve leaflets. According to the approaches described herein, functional tricuspid valve regurgitation is treated by selectively introducing circumferential tension around the valve annulus to retard dilation. One goal is to augment the effective (forward) right ventricular stroke volume by reducing regurgitant (backward) right ventricular stroke volume. Specifically, the septal-lateral dimension of the tricuspid valve annulus is reduced by extracardiac force or pressure applied through a tensioning element (such as, e.g., a suture) usually in combination with a separate compression member. The tensioning element is positioned generally along the atrioventricular groove and tightened to increase force exerted through the compression member on a desired treatment area.

As mentioned above, the compression member is used in conjunction with the tensioning element to enhance the force applied at one or more selected areas. The compression member may be designed to preferentially deform as tension is increased in the tensioning element.

As also described above, another kind of member, called a protection member, may be introduced to protect certain vital structures, e.g., blood vessels, within the tensioning element from being deformed by the forces applied by the tensioning element. The functions of compression members and protection members may be combined in some applications.

In addition to tricuspid valve repair, related approaches are aimed at addressing congenital heart disease by providing an extracardiac force to compress the right ventricular outflow tract or pulmonary artery trunk in conjunction with or instead of surgical banding.

III. Embodiments

FIG. 1 is an anatomical schematic cross section of the heart viewed from above. As shown in FIG. 1 and described above, functional tricuspid valve regurgitation or "leakage" results when the free wall of the tricuspid valve dilates. Tricuspid valve annuloplasty, or repair of the heart valve, can be achieved by restricting the dilation of the free wall, which enhances coaptation of the tricuspid valve leaflets.

Figure 2:
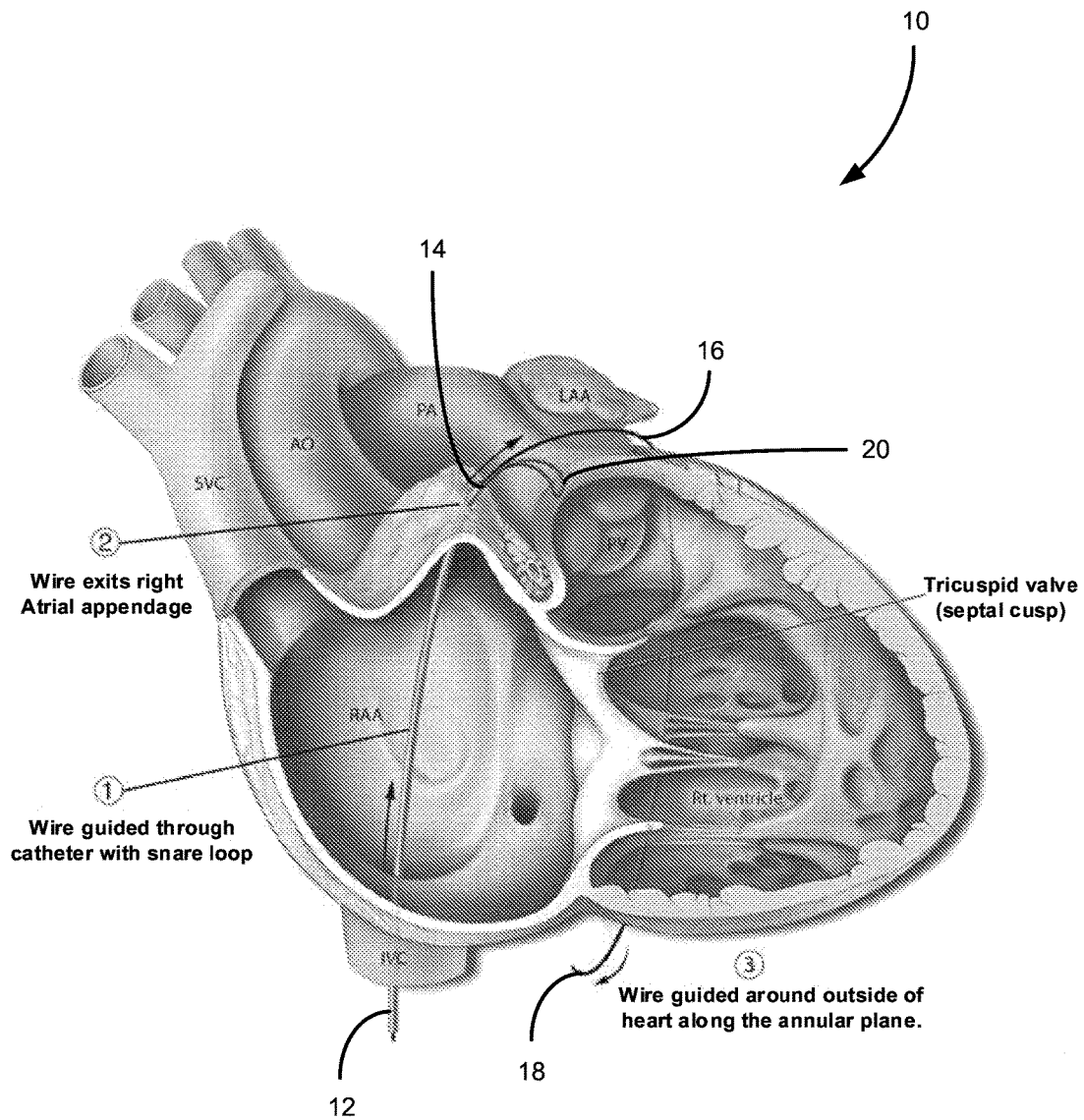
FIG. 2 is a partial cross-sectional view of an anterior of a human heart showing a catheter extending from the right atrial appendage, a distal end of a flexible member extending from the catheter and around the heart and a capture loop for receiving the distal end of the flexible member.

FIG. 2 depicts a catheter 12 that has been inserted from the femoral vein and directed to penetrate the right atrial appendage to exit the right atrial cavity and enter the pericardial or extracardiac space. A flexible member 16, sometimes referred to as a wire, is inserted through a sheath of the catheter, and is shown extending beyond a tip 14 of the catheter. A distal end 18 of the flexible member 16, which is the free end, is directed around the heart, such as in the "clockwise" direction as shown by the arrows. The path of the flexible member 16 as shown in FIG. 2 is generally along or near the atrioventricular groove on the exterior of the heart.

A capture loop 20 is provided, such as attached to the flexible member 16 and spaced from its distal end 18. Alternatively, the capture loop 20 can be provided on a dedicated flexible member that is separate from the flexible member 16.

Figures 3A, 3B:
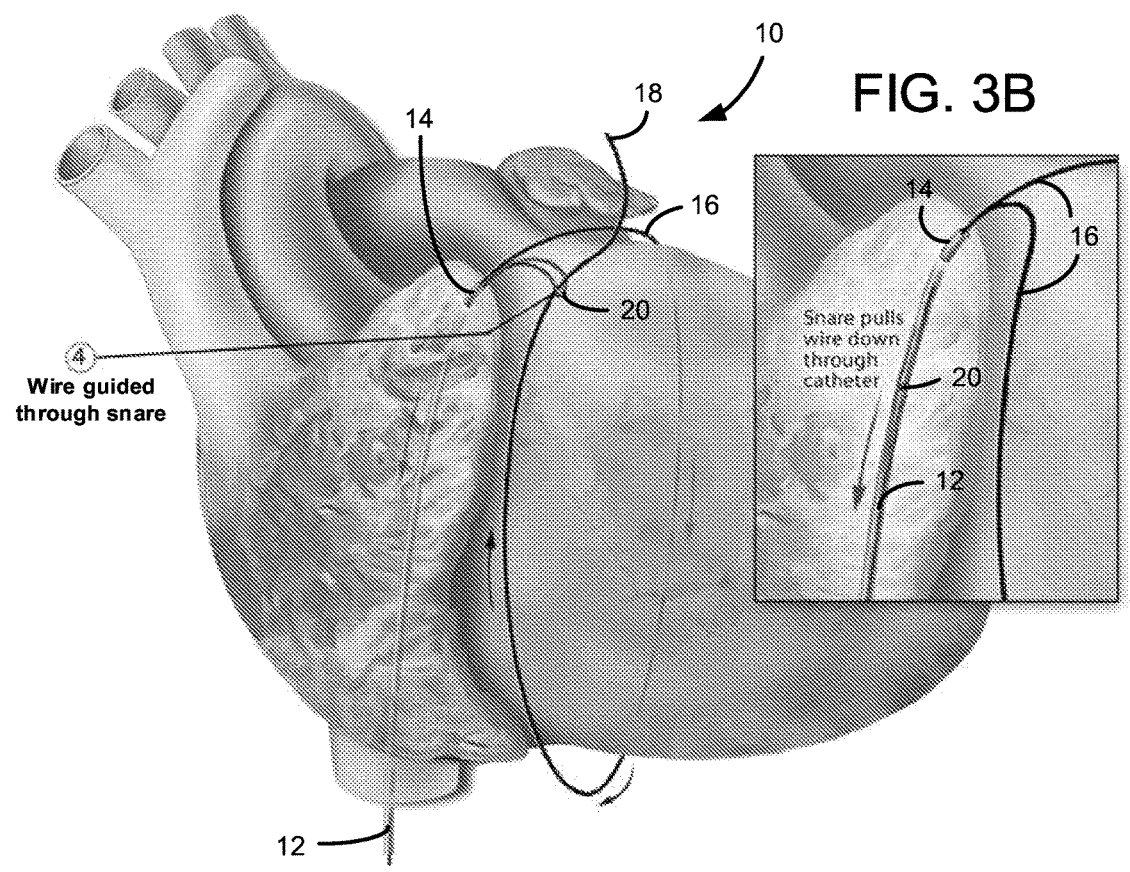
FIG. 3A is an elevation view of the anterior of the heart of FIG. 2 showing that the flexible member has been guided through the capture loop.
FIG. 3B is an enlarged perspective of the catheter at the right atrial appendage showing that the distal end of the flexible member has been cinched around the heart and withdrawn into the catheter.

As shown in FIG. 3A, the distal end 18 of the flexible member 16 can be routed around the heart and through the capture loop 20. Thereafter, the flexible member 16 can be withdrawn with the distal end 18 engaged with the capture loop 20 into and back through the catheter, as shown in FIG. 3B. The flexible member 16 can be replaced with a tensioning element 17 (see, e.g., FIG. 4), by attaching the tensioning element 17 to the flexible member 16 with the tensioning member 17 being pulled into place as the flexible member 16 is withdrawn. Tension is then increased in the tensioning member 17. A suitable capture device (the capture loop 20 being just one example) can be used to grasp the tensioning element 17 and to manipulate it as desired to effect the required tension. In this way, the circumferential tension around the heart exerted by the tensioning member causes the tricuspid valve annulus to shorten radially and enhances its coaptation. Thus, this approach can be described as providing extracardiac circumferential tension by a member or device delivered via a transatrial intrapericardial catheter.

Figure 4:
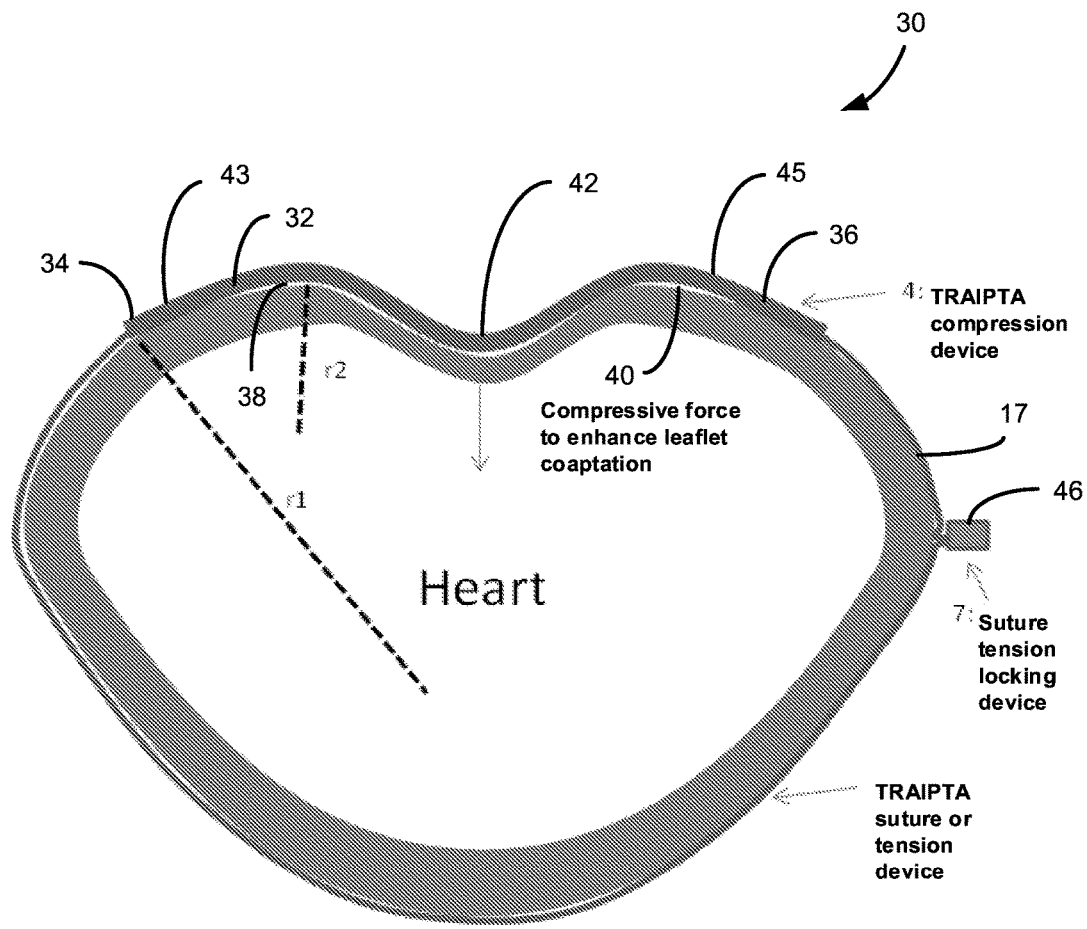
FIG. 4 is a schematic cross-section of the heart after the flexible member has been tensioned around the heart and over a compression member that applies force to the heart in predetermined areas.

FIG. 4 is a schematic view of a cross-section of the heart showing the location of the tensioning element 17 having been "pulled" into the location previously occupied by the flexible member 16, which has been withdrawn. As also shown in FIG. 4, there can be a knot or a locking mechanism, such as the lock 46 on the flexible member 16, set to "lock" or fix the tensioning element 17 in place once it has been cinched to a desired degree to provide the predetermined force.

In FIG. 4, a compression member 30 designed to work in conjunction with the tensioning element 17 is shown. Specifically, the compression member 30 is positioned between the heart and the tensioning element 17 such that it bears against the compression member 30 when it is tightened around the heart. In the case of the tensioning element 17 alone (or the flexible member 16 alone, as in some embodiments) and assuming a uniform construction thereof, the pressure exerted on the heart is fairly uniform throughout the closed loop encircling the heart. The compression member 30, however, is designed to cause greater force to be exerted on the heart as desired in areas where it is located.

Figure 8A:
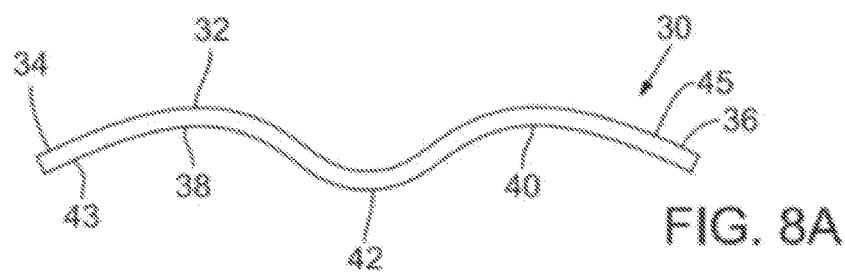
FIG. 8A is a side elevation view of the compression member of FIG. 4.

The compression member 30 of FIG. 4 is also shown in FIG. 8A for greater clarity. As shown in FIGS. 4 and 8A, the compression member 30 has a body 32, a first end 34 and a second end 36. The body 32 has a contoured shape to follow the outer periphery of the heart and to apply force to the heart at desired locations.

In the specific implementation shown, the body 32 can be described as having a shaped profile along its length. More specifically, the body has an "M"-shaped profile, with a first arch 38 adjacent the first end 34, and a second arch 40 adjacent the second end 36. Between the first arch 38 and the second arch 40 in the illustrated implementation, there is a bulge 42 that is positionable to apply greater force to a selected location, in this case to the tricuspid valve area.

Segments 43, 45, which extend from the first end 34 to the peak of the first arch 38 and from the second end 36 to the peak of the second arch 40, are shaped to follow the contours of areas of the heart against which they are designed to be positioned. These segments are referred to as lateral segments, and they tend to promote self-righting of the compression member 30 into a position parallel to the plane of the valve annulus as tension is applied through the tensioning element 17 to draw the compression member and segments 43, 45 into contact against the areas of the heart. Stated differently, these segments help the compression member adopt a position normal to the surface against which it is pressed when tension is applied. The compression member is generally self-orienting when tension is applied to it ends, which allows it to be pulled into position while maintaining a predictable position and then to exert force against the heart as desired.

The contoured shape or shaped profile of the body 32 may be described with one or more radii of curvature. Referring to FIG. 4, segments 43, 45 of each arch 38, 40 from its respective end 34, 36 to its peak can have a large radius of curvature r1. The remainder of each arch 38, 40, from its peak towards its inner end can have a smaller radius of curvature r2. The larger radius of curvature r1 conforms to the heart's surface, whereas the smaller radius of curvature r2 imparts a geometric reduction on a surface against which it bears.

By choice of materials or geometry, one or more segments of the compression member 30 may be designed to deform more easily or preferentially than other segments of the compression member 30.

Figure 8B:
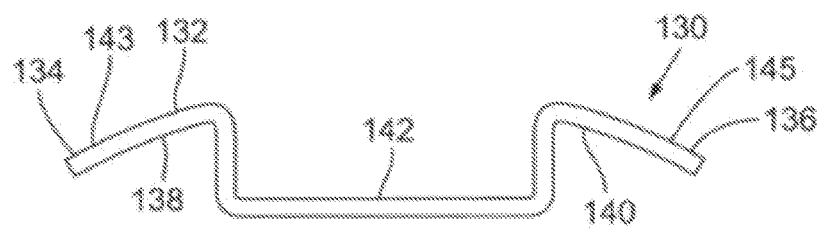
FIG. 8B is a side elevation view of an alternative compression member having a relatively straight center segment.
Figure 8C:
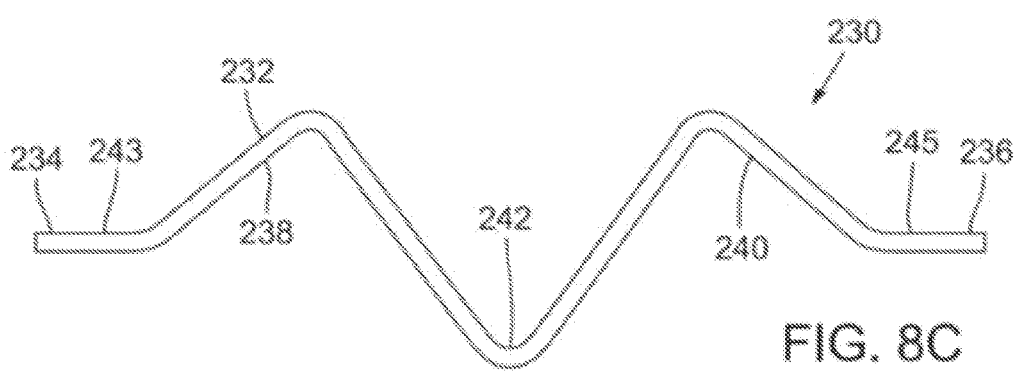
FIG. 8C is a side elevation view of an alternative compression member having a center segment with a vertex.

Representative alternative compression members are shown in FIGS. 8B and 8C. In contrast to the bulged center segment 42 of the compression member 30, a compression member 130 has a generally straight center segment 142. The straight section 142 allows force to be applied along a larger area of the heart than can be applied with the bulge 42. The compression member 130 has more pronounced changes in direction between the center section 142 and the adjoining arched sections 138, 140. Lateral segments 143, 145 (sometimes referred to as end segments because they extend inwardly from the ends 134, 136, respectively) tend to promote the self-righting of the compression member 130 when tension is applied.

Referring to FIG. 8C, a compression member 230 is more angled than the curved compression member 30. The compression member 230 can be described as having four or more bends. In the compression member 230, arched sections 238, 240 are mostly angled rather than fully curved. The compression member 230 has a center segment with a vertex 242 providing a pronounced point of focus for the application of force to the heart.

In the illustrated implementation, the various compression members have a grooved and/or tubular construction, or have eyelets, shaped to receive the tensioning element 16, thus coupling the compression member to the tensioning element 17 (or the flexible member 16). The various compression members described herein can be formed as a single piece, or it may comprise multiple segments that are assembled together in situ, (i.e., adjacent the treatment area within the body). Providing the compression member in multiple pieces may facilitate its introduction into the body through a catheter. Each compression member can have grooves or other patterning, such as on its inner surface, to enhance its "grip" in the treatment area.

Figures 5A, 5B:
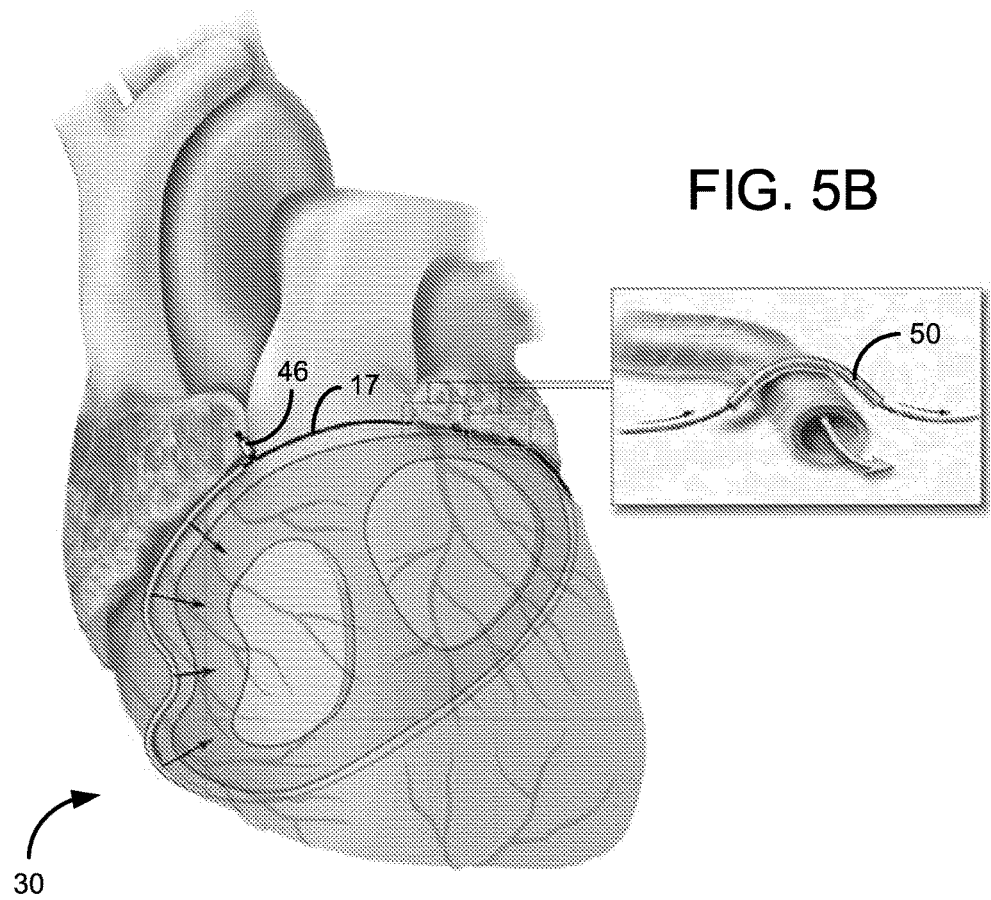
FIG. 5A is another elevation view of the anterior of the heart showing the compression member of FIG. 4 in place over the tricuspid area of the heart and two protection devices in place over coronary artery segments.
FIG. 5B is an enlarged perspective view of one of the protection members of FIG. 5A in place over the corresponding coronary artery segment.

FIG. 5A shows the compression member 30 in place and bearing against the tricuspid annulus after the flexible member has been cinched as desired. Specifically, the bulge 42 is oriented to apply greater force along the edge of the tricuspid annulus where dilation is greatest. The applied force to the anterior and posterior walls of the tricuspid annulus enhances leaflet coaptation.

As shown in FIG. 5A, and as best seen in FIG. 5B, a protection member 50 can be provided to protect certain structures from being deformed under the force applied by the flexible member 16. The protection member 50 can have a curved shape that defines a protected space 52 as shown in FIG. 5B. The protection member 50 can be positioned as shown with a left coronary artery (or other vital structure) received in the protected space 52. In this way, the coronary artery is protected from unintended deformation as the tensioning element is cinched tight to provide the appropriate force on the compression member. In the example of FIG. 5A, two such protection members are in use, but any number can be used.

As also shown in FIG. 5A, the compression member 30 can be provided with anti-slip features such as barbs 33 that tend to engage with the adjacent surface of the heart when the compression member 30 is forced against the heart by the tension in the tensioning element 17. The illustrated barbs 33 are exemplary, and they can be provided over more or less of the length of the compression member.

Figure 6:
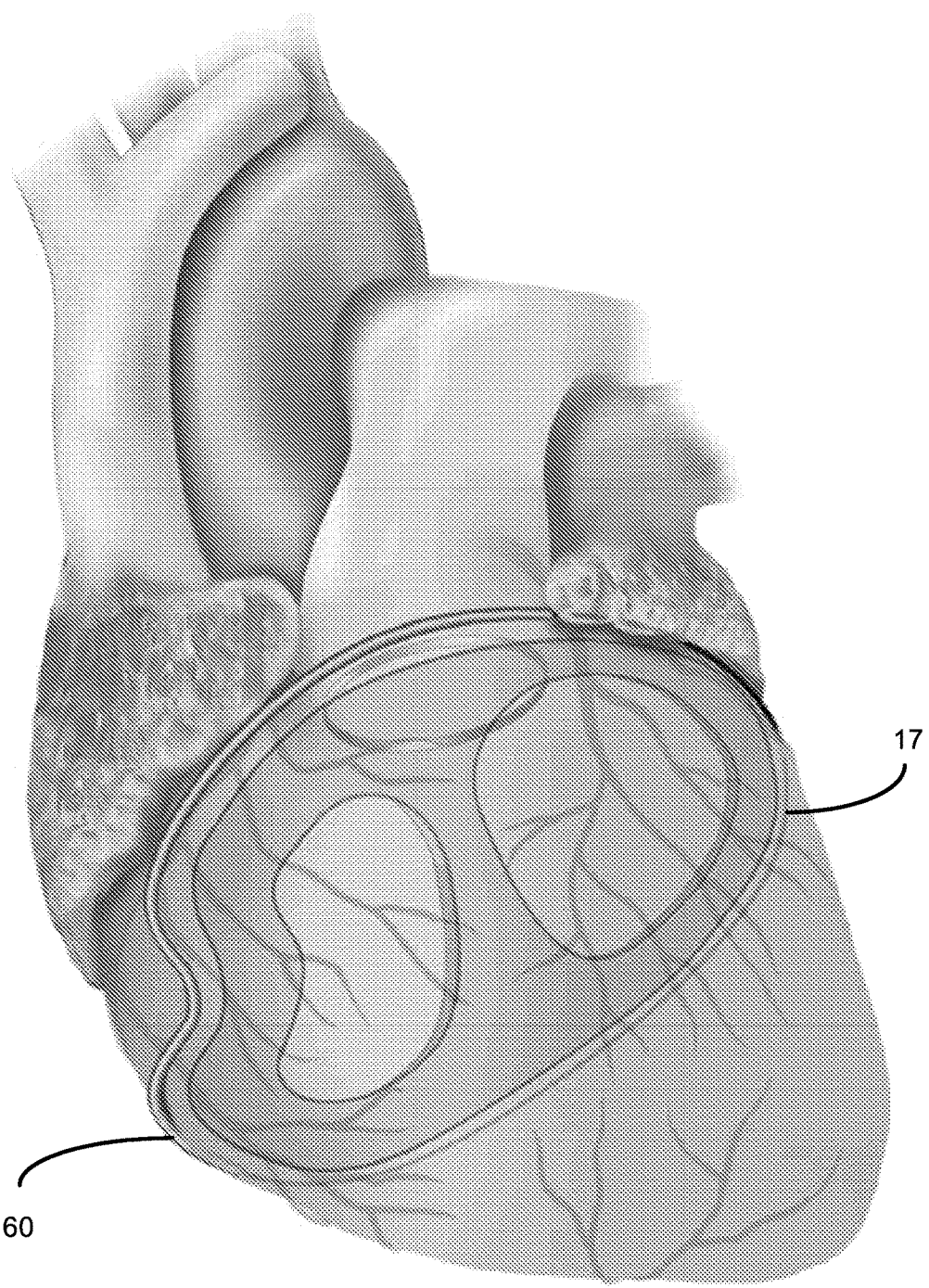
FIG. 6 is another view of the anterior of the heart showing another compression member in place to protect the right ventricle outflow tract (RVOT).

FIG. 6 shows an alternative implementation that is similar to FIG. 5A, but includes a compression member 60 instead of the compression member 30. The compression member 60 is shaped to occupy a longer portion of the periphery of the heart than the compression member 30. By selecting the proper geometry and size, the compression member 60 can be positioned as shown to provide the desired force on the tricuspid annulus, and also to extend over and protect the right ventricle outflow tract and/or coronary arteries from undesirable compression.

Figure 7:
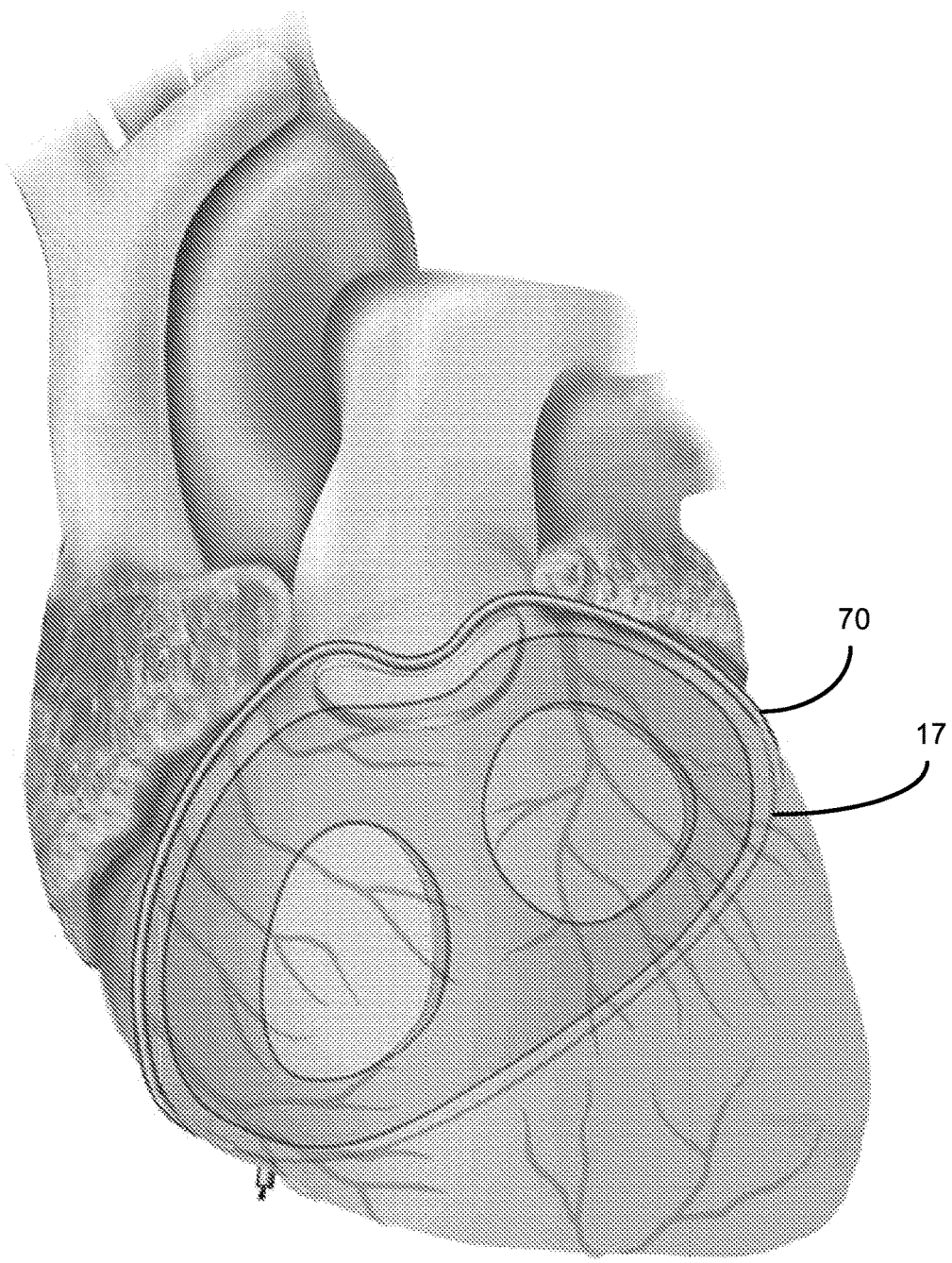
FIG. 7 is another view of the anterior of the heart showing another compression member in place on the pulmonary artery to provide resistance to flow.

FIG. 7 shows an alternative implementation that is similar in some aspects to FIGS. 5A and 6, but instead includes a compression member 70 having a bulge designed to apply pressure to the right ventricular outflow tract or pulmonary artery trunk to create intended compression and thereby temporary resistance to blood flow as part of staged correction/palliation of congenital heart disease, in place of surgical "pulmonary artery banding." As can be seen in FIG. 7, the compression member 70 also has a greater length than the compression member 30 and includes long protection arches, e.g., 3-6 mm in length.

The various members 30, 130, 230, 50, 60 and 70 can be constructed of stainless steel, nitinol or any other suitable material. The members are preferably dimensioned for introduction to the treatment area via a catheter. Members that are resilient, elastic, or superelastic, it can be designed for delivery via a low-profile catheter. In addition, such members can be bound into a smaller size for easier delivery and then allowed to expand before deployment. Larger members may require delivery via a large-bore catheter. In addition, any of the members may be a provided as multiple-piece assemblies of components where the components are small enough for delivery via a catheter. The resulting member may be self-assembled in situ. In one example, the segments are beads having notches or other shapes that fit together to allow assembly into one member.

Members can be provided in different sizes based on the differences in typical tricuspid valve geometry. In addition, customized or bespoke members can be made based on measurements derived from cardiac imaging procedures such as angiography, ultrasound, computed tomography and/or magnetic resonance imaging.

Example 1

In an exemplary procedure, the following steps are performed:

1. From a transfemoral vein approach, position a catheter in the right atrial appendage.
2. Exit the right atrial appendage into the pericardial space using appropriate imaging guidance, and using a suitable catheter device, such as a Brockenbrough needle, an introducer sheath dilator, and/or a stiff guidewire (flexible member).
3. Introduce an access sheath from the femoral vein into the pericardial space.
4. Position a capture device (e.g., a snare or other type of capture device) in the pericardial space, or use a customized capture device integrated into the access sheath.
5. Navigate a distal end of a guidewire "clockwise" (viewed from below) around the base of the heart and into the capture device or snare.
6. Capture the guidewire and provide access to a free end of the guide wire.
7. Introduce one or more compression and protection devices over the guidewire.
8. Reposition the guidewire into the appropriate position with regard to the target structures (tricuspid valve, coronary arteries, RVOT, etc.) using imaging guidance and the access sheath.
9. Position the compression and protection devices using imaging guidance.
10. Withdraw guidewire to apply tension, or withdraw guidewire to position tensioning element and then apply tension.
11. Assess for reduction in tricuspid regurgitation, for freedom from coronary artery compression, and for freedom from MPA/RVOT compression, using any combination of ultrasound, MRI, and X-ray angiography.
12. Provide stimulation (pharmacologic or otherwise) to alter loading conditions and inotropic state as desired, under imaging guidance, to assure suitable application of therapeutic compression to the intended cardiac structure under "stressed" conditions.
13. Deliver and apply tension fixation device (e.g., a lock) or form a knot in tensioning element.
14. Deliver and apply atrial exit site closure, whether part of tension fixation device or a separate occluder which can be made of non-absorbable (e.g. Nitinol) or absorbable material device that provides for affixing patches on one or both sides of a heart surface to close an opening in the heart surface.
15. Assess for freedom from complications, address as needed.
16. Obtain vascular hemostasis.

In alternative procedures or methods, any one or more of these listed acts can be performed without performing others of these listed acts, and in such methods these acts can be performed alone or in combination with other acts, and the acts can be performed in the order given above or in other orders.

The described approaches provide for addressing functional tricuspid valve regurgitation and other similar heart conditions with minimally invasive surgery that does not require cardiopulmonary bypass or open heart surgery techniques.

In addition to the approaches described above, it is also possible to configure the devices and adapt the methods for transthoracic delivery of the tensioning element, as well as any compression member or protection member that may be used.

In view of the many possible embodiments to which the disclosed principles may be applied, it should be recognized that the illustrated embodiments are only preferred examples and should not be taken as limiting in scope. Rather, the scope of protection is defined by the following claims.

The invention claimed is:

1. A device for applying force to an area of a patient's heart along or near the atrioventricular groove, comprising:
   a flexible member configured to be guided through a catheter and positioned around the heart generally along or near the atrioventricular groove;
   a capture loop configured to extend from the catheter and snare an end of the flexible member that extends around the heart, and configured to pull the snared end of the flexible member back into the catheter;
   a tensioning element configured to be delivered by the flexible member around the heart generally along or near the atrioventricular groove; and
   a compression member positionable along the tensioning element and over a desired segment of the atrioventricular groove to develop force to be applied to an adjacent area of the heart by selective tensioning of the tensioning element.

2. The device of claim 1, wherein the tensioning element or the compression member is deliverable through a catheter through the right atrium or right atrial appendage of the heart.

3. The device of claim 1, wherein the tensioning element or the compression member is deliverable through a catheter inserted along a trans-thoracic or subxiphoid path.

4. The device of claim 1, wherein the compression member is positionable along the tensioning element by using a wire or cable securable to the compression device to move the compression device relative to the tensioning element.

5. The device of claim 1, wherein the compression member is tubular and defines a bore dimensioned to allow the tensioning element to pass through the compression member.

6. The device of claim 1, wherein the compression member has a groove dimensioned to receive the tensioning element and to assist in retaining contact between the tensioning element and the compression member.

7. The device of claim 1, wherein the compression member has at least one anti-slip feature configured to contact a surface of the heart to reduce slipping of the compression member relative to the heart when the compression member is in position with tension applied to the tensioning element.

8. The device of claim 7, wherein the anti-slip feature comprises protruding barbs configured to grip an exterior surface of the heart.

9. The device of claim 1, wherein the compression member has a shaped profile along its length.

10. The device of claim 9, wherein the shaped profile comprises an M-shaped section.

11. The device of claim 9, wherein the shaped profile comprises at least two inflection points between segments of different curvatures.

12. The device of claim 9, wherein the shaped profile comprises a generally straight center segment.

13. The device of claim 9, wherein the shaped profile comprises a center segment having a vertex.

14. The device of claim 1, wherein the compression member has end segments shaped to orient the compression member.

15. The device of claim 1, wherein the compression member is self-orienting upon application of tension in a selected location for treatment.

16. The device of claim 1, wherein the compression member is comprised of multiple component parts separately deliverable through the catheter and configured to be assembled together at or near a treatment site.

17. The device of claim 1, wherein the compression member is resiliently deformable such that the compression member changes from a delivery shape suitable for delivery through the catheter to a final shape after delivery to a treatment site.

18. The device of claim 1, further comprising a protection member shaped to provide a protected space adapted to at least partially accommodate the pulmonary artery, the left atrium, an other blood vessel, or an other vital structure, and adapted to receive the tensioning element, wherein the protection member distributes force developed through increased tension in the tensioning element to either side of the protected space.

19. A method of applying force to an area of a patient's heart along or near the atrioventricular groove, comprising:
positioning a tensioning element around the heart and generally along the heart's atrioventricular groove;
using a catheter to deliver a compression member through the right atrium or right atrial appendage of the heart;
positioning the compression member along the tensioning element and over a desired treatment location; and
applying force to the desired treatment location with the compression element by applying tension with the tensioning element.

20. The method of claim 19, further comprising using imaging guidance to ascertain positions of at least one of the compression member, the tensioning element, and a catheter for delivering the compression member or the tensioning element.

21. The method of claim 19, wherein the tensioning element interacts with the compression element to urge the compression element into a position normal to the treatment location as tension is increased.

22. The method of claim 19, further comprising delivering the compression member through a catheter and through an opening in the right atrial appendage.

23. The method of claim 19, further comprising delivering multiple compression member components to the treatment area and assembling the compression member components into the compression member.

24. The method of claim 19, further comprising positioning at least one protection member along a segment of the tensioning element, the at least one protection member being shaped to provide a protected space at least partially accommodating a blood vessel or other vital structure.

25. A method of applying force to an area of a patient's heart along or near the atrioventricular groove, comprising:
positioning a tensioning element around the heart and generally along the heart's atrioventricular groove;
delivering a compression member through a catheter and through an opening in the right atrial appendage;
positioning the compression member along the tensioning element and over a desired treatment location; and
applying force to the desired treatment location with the compression element by applying tension with the tensioning element.

26. The method of claim 25, further comprising using imaging guidance to ascertain positions of at least one of the compression member, the tensioning element, and a catheter for delivering the compression member or the tensioning element.

27. The method of claim 25, wherein the tensioning element interacts with the compression element to urge the compression element into a position normal to the treatment location as tension is increased.

28. The method of claim 25, further comprising delivering multiple compression member components to the treatment area and assembling the compression member components into the compression member.

29. The method of claim 25, further comprising positioning at least one protection member along a segment of the tensioning element, the at least one protection member being shaped to provide a protected space at least partially accommodating a blood vessel or other vital structure.

* * * * *